(12) United States Patent
Gaillot et al.

(10) Patent No.: US 10,967,129 B2
(45) Date of Patent: Apr. 6, 2021

(54) DOSING DEVICE

(71) Applicant: HOFFMANN-LA ROCHE INC., Little Falls, NJ (US)

(72) Inventors: Maxime Gaillot, Basel (CH); Roberta Leah, Basel (CH); Declan Reilly, Basel (CH); Mark Digby Teucher, Bath (GB); Paul Graham Hayton, Bristol (GB); Jonathan Paul Ridley, Bristol (GB); James Robert Coop, Bristol (GB)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 255 days.

(21) Appl. No.: 16/062,016

(22) PCT Filed: Dec. 13, 2016

(86) PCT No.: PCT/EP2016/080826
§ 371 (c)(1),
(2) Date: Jun. 13, 2018

(87) PCT Pub. No.: WO2017/102745
PCT Pub. Date: Jun. 22, 2017

(65) Prior Publication Data
US 2018/0361074 A1 Dec. 20, 2018

(30) Foreign Application Priority Data

Dec. 14, 2015 (EP) ..................................... 15199909
Dec. 14, 2015 (EP) ..................................... 15199911
(Continued)

(51) Int. Cl.
*A61M 5/315* (2006.01)
*A61M 5/20* (2006.01)
(Continued)

(52) U.S. Cl.
CPC ................ *A61M 5/204* (2013.01); *A61J 1/20* (2013.01); *A61J 1/2006* (2015.05); *A61J 1/2096* (2013.01);
(Continued)

(58) Field of Classification Search
CPC .............. A61M 5/204; A61M 5/31571; A61M 5/3213; A61M 5/31561; A61M 5/3158;
(Continued)

(56) References Cited

U.S. PATENT DOCUMENTS 4,583,978 A  4/1986 Porat et al.
5,582,598 A  12/1996 Chanoch
(Continued)

FOREIGN PATENT DOCUMENTS

EP  02292286 A1  3/2011
JP  H08103495  4/1996
(Continued)

OTHER PUBLICATIONS

International Search Report dated Feb. 24, 2017 in corresponding International Patent Application No. PCT/EP2016/080826.
(Continued)

*Primary Examiner* — Laura A Bouchelle
*Assistant Examiner* — Anh Bui
(74) *Attorney, Agent, or Firm* — Medler Ferro Woodhouse & Mills PLLC

(57) ABSTRACT

A dosing device includes a rod element and a shell. The rod element has a stem with a longitudinal axis and a first thread arrangement. The shell has a second thread arrangement. The first thread arrangement of the rod element or the second thread arrangement of the shell includes a thread. The first thread arrangement of the rod element and the second thread arrangement of the shell engage. The rod element is movable along the longitudinal axis of its stem by rotating the shell (Continued)

and the rod element relative to each other causing the first thread arrangement of the rod element and the second thread arrangement of the shell to travel along each other. A dosage chamber is formed by moving the rod element along the longitudinal axis of its stem. The volume of the dosage chamber is varied by moving the rod element along the longitudinal axis of its stem. An inclination angle ($\alpha$, $\beta$) of the thread varies along the thread. The dosing device according to the invention can allow for a precise and convenient dosing of a liquid out of a container. In particular, it can allow for efficiently dosing a comparably small volume out of a comparably large container.

18 Claims, 4 Drawing Sheets

(30) Foreign Application Priority Data

| Dec. 14, 2015 | (EP) | 15199913 |
| Dec. 14, 2015 | (EP) | 15199915 |
| May 3, 2016 | (EP) | 16167999 |

(51) Int. Cl.
| *A61M 5/178* | (2006.01) |
| *A61J 1/20* | (2006.01) |
| *A61M 5/32* | (2006.01) |
| *A61M 5/24* | (2006.01) |
| *A61M 5/31* | (2006.01) |

(52) U.S. Cl.
CPC ............ *A61M 5/1782* (2013.01); *A61M 5/20* (2013.01); *A61M 5/2422* (2013.01); *A61M 5/3146* (2013.01); *A61M 5/3158* (2013.01); *A61M 5/31505* (2013.01); *A61M 5/31525* (2013.01); *A61M 5/31528* (2013.01); *A61M 5/31536* (2013.01); *A61M 5/31551* (2013.01); *A61M 5/31553* (2013.01); *A61M 5/31561* (2013.01); *A61M 5/31571* (2013.01); *A61M 5/3213* (2013.01); *A61M 2005/3126* (2013.01); *A61M 2205/58* (2013.01); *A61M 2205/581* (2013.01); *A61M 2205/582* (2013.01); *A61M 2205/583* (2013.01)

(58) Field of Classification Search
CPC ................ A61M 5/31536; A61M 5/20; A61M 5/31551; A61M 5/31505; A61M 5/3146; A61M 5/2422; A61M 5/1782; A61M 5/31553; A61M 5/31528; A61M 5/31525; A61M 2205/582; A61M 2205/581; A61M 2205/583; A61M 2005/3126; A61J 1/2006; A61J 1/2096; A61J 1/20
See application file for complete search history.

(56) References Cited

U.S. PATENT DOCUMENTS

| 6,607,508 | B2 | 8/2003 | Knauer | |
| 2001/0037087 | A1* | 11/2001 | Knauer | A61M 5/204 |
| | | | | 604/137 |
| 2011/0270222 | A1 | 11/2011 | Wei et al. | |
| 2012/0310206 | A1* | 12/2012 | Kouyoumjian | A61M 5/31543 |
| | | | | 604/506 |
| 2018/0200442 | A1* | 7/2018 | Atterbury | A61M 5/2033 |

FOREIGN PATENT DOCUMENTS

| JP | 2013503669 A | 2/2013 |
| JP | 2015531258 A | 11/2015 |
| WO | 01/52920 A2 | 7/2001 |
| WO | 2010/139671 A1 | 12/2010 |
| WO | 2011/095488 A1 | 8/2011 |
| WO | 2012/143437 A1 | 10/2012 |
| WO | 2014040929 A1 | 3/2014 |
| WO | 2015032772 A1 | 3/2015 |

OTHER PUBLICATIONS

Written Opinion dated Feb. 24, 2017 in corresponding International Patent Application No. PCT/EP2016/080826.
Japanese Office Action dated Nov. 18, 2020 in corresponding Japanese Patent Application No. 2018-530703.
Japanese Search Report dated Nov. 10, 2020 in corresponding Japanese Patent Application No. 2018-530703.

* cited by examiner

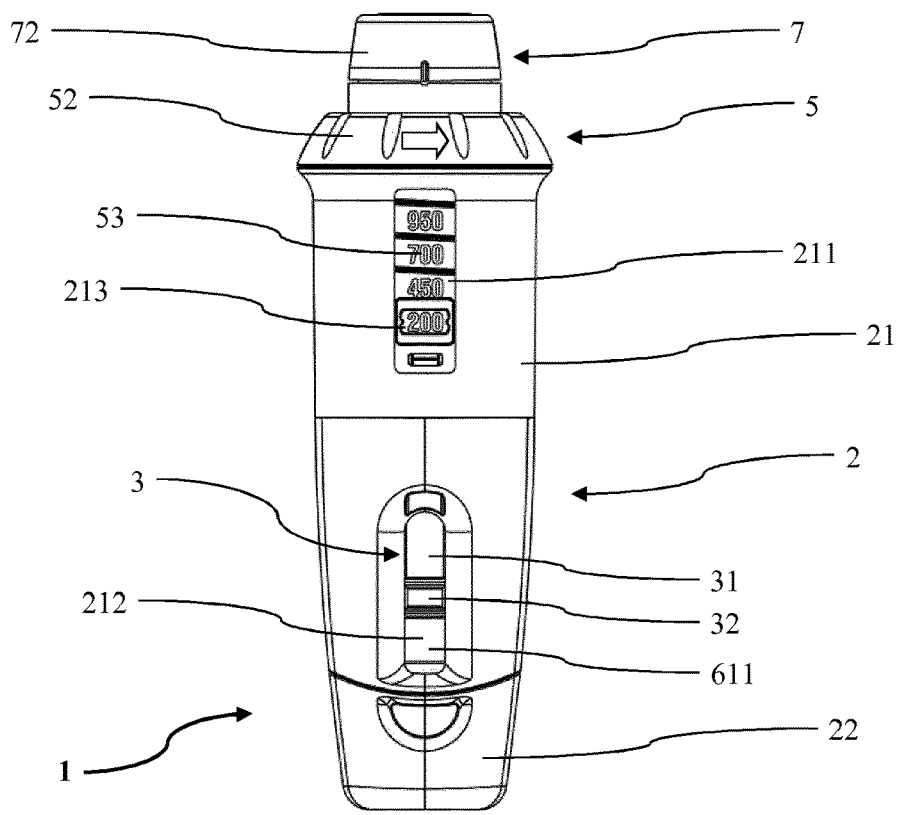
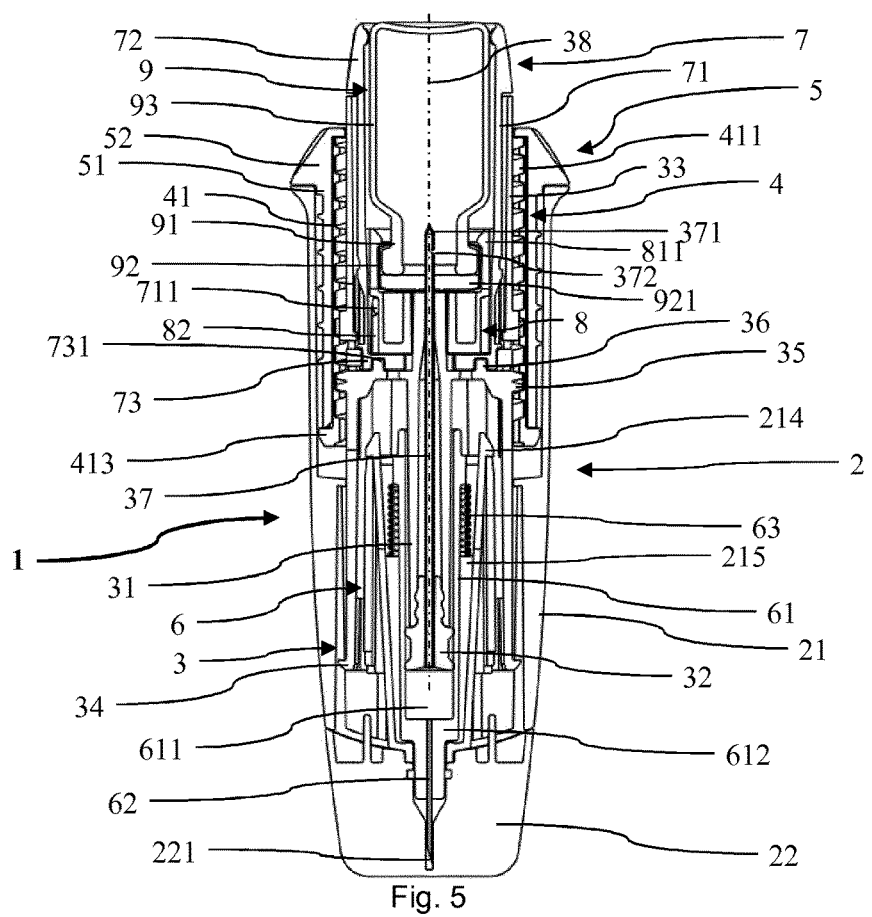
Fig. 4
Fig. 5

DOSING DEVICE

TECHNICAL FIELD

The present invention relates to a dosing device according to the preamble of independent claim 1. Such a device can comprise a rod element having a stem with a longitudinal axis and a first thread arrangement, and a shell having a second thread arrangement. The first thread arrangement of the rod element or the second thread arrangement of the shell comprises a thread. The first thread arrangement of the rod element and the second thread arrangement of the shell engage. The rod element is movable along the longitudinal axis of its stem by rotating the shell and the rod element relative to each other causing the first thread arrangement of the rod element and the second thread arrangement of the shell to travel along each other. A dosage chamber is formed by moving the rod element along the longitudinal axis of its stem and the volume of the dosage chamber is varied by moving the rod element along the longitudinal axis of its stem. Devices of this kind can be used by a patient or other user for dosing a specific amount of a medicament for self-administration.

BACKGROUND ART

Dosing a liquid or other fluid from a container is required in many medical, clinical or other applications and performed in a plurality of different ways. For example, liquid pharmaceutical substances or medicaments are often provided in glass or plastic vials or containers which are closed by a septum or rubber plug and a metal cap clamped around it or another similar seal cover. Particularly, where it is essential that the liquid is comparably precisely provided such as in pharmaceutical or therapeutic applications, specific devices are commonly used for dosing.

Conventionally, for delivering medicaments out of vials, syringes are used. Thereby, a needle attached to the syringe penetrates the septum or cover and the pharmaceutical substance is withdrawn into the syringe through the needle. Dosing is manually performed by visually controlling the withdrawal of the medicament into the syringe. Once transferred into the syringe, the medicament can be delivered in an appropriate manner. For example, the medicament can be, e.g. subcutaneously or intramuscularly, injected from the needle into a patient or it can be orally applied or provided as droplets, e.g., in the eyes, mouth or nose of the patient. However, particularly where it is required to precisely dose a specific amount of medicament or where comparably small volumes such as in a range of ten microliter to about one milliliter are to dose it usually is necessary that an educated person such as a doctor or a nurse is involved. In such cases patients are often not capable of performing the delivery themselves when using a regular syringe or a similar device, i.e. self-administration is not possible. However, self-administration of liquids or medicaments is beneficial in many therapeutic applications since the effort for the patient and the costs of the therapy can be extensively reduced.

For improving this situation, there are devices used which allow for more conveniently delivering a comparably precise volume of liquids. For example, U.S. Pat. No. 6,607,508 B2 describes an automatic medicament delivery device having a cylindrical syringe barrel into which a plunger rod extends from one side. The other side of the syringe barrel is equipped with a thread onto which a needle assembly can be screwed. The plunger rod has a vial seat into which a vial can be snapped in. The plunger rod is further equipped with a pathway longitudinally extending throughout the entire plunger rod. Radially from the plunger rod pins extend which inter-engage with slots of a dose barrel surrounding the section of the plunger rod having the pins. By turning the dose barrel via a dose ring the plunger rod translates and a volume is created between the plunger rod and the thread side of the syringe barrel. Induced by this movement a medicament is transferred from the vial through the pathway into the volume. The turning of the dose barrel into an opposite direction is blocked by a ratchet mechanism which ensures that no liquid can be pressed back through the pathway.

The known devices used for dosing involve the problem that in an initial phase air is present in the system which is included in the dosing process. Particularly, when a comparably small volume from a comparably large container is to be dosed such air in the system makes a careful dosing and additional steps necessary. For example, initially the air can be inside the needle and the initial volume of a dosage chamber. Thus, in the initial phase the air typically is withdrawn from the needle into the dosage chamber and only later the liquid follows. In syringes or similar devices such air can make it necessary to prime the syringe prior delivery. In particular, it can be necessary to eject the air out of the system before injection. Additionally, the dosing itself can be comparably cumbersome since in the beginning the air is dosed. For example, in rotational dosing as described above the first rotational movements are not providing liquid into the dosage chamber but air only. After all air is in the dosage chamber suddenly the liquid follows which can surprise the user of the device and decrease the accuracy of the dosing.

Therefore, there is a need for a dosing system allowing a precise and convenient dosing of a liquid out of a container.

DISCLOSURE OF THE INVENTION

According to the invention this need is settled by a dosing device as it is defined by the features of independent claim 1. Preferred embodiments are subject of the dependent claims.

In particular, the invention deals with a dosing device which comprises a rod element and a shell. The rod element has a stem with a longitudinal axis and a first thread arrangement. The shell has a second thread arrangement. The first thread arrangement of the rod element or the second thread arrangement of the shell comprises a thread. The first thread arrangement of the rod element and the second thread arrangement of the shell engage. The rod element is movable along the longitudinal axis of its stem by rotating the shell and the rod element relative to each other causing the first thread arrangement of the rod element and the second thread arrangement of the shell to travel along each other. A dosage chamber is formed by moving the rod element along the longitudinal axis of its stem and the volume of the dosage chamber is varied or adapted by moving the rod element along the longitudinal axis of its stem. An inclination angle of the thread of the first thread arrangement of the rod element or the second thread arrangement of the shell varies along the thread of the first thread arrangement of the rod element or the second thread arrangement of the shell.

The term "thread" as used herein relates to a male structure such as a ridge or a female structure such as a groove extending along and around a surface or body. Typically threads are helically or essentially helically shaped and run along and around a body or part.

The shell can be embodied as a dial shell such that it can be manually rotated. For example, such a dial shell can be essentially cylindrically shaped or comprise plural segments such as cylinder segments. It can also be embodied as one or plural arms equipped with a structure such as, e.g., a pin for engaging the thread. In particular, the shell can be designed to be arranged adjacent to the second thread arrangement.

The rod element can comprise a stopper at its proximal end side. In particular, the stopper can be located at a proximal end side of the stem of the rod element. The term "stopper" in this context can relate to a stopper in the narrow sense, i.e. a plug-like sealing member. It can also relate to alternative sealing members such as O-rings mounted to the stem or the like. The stopper can be made of an elastic material such as a rubber in order to comply providing tightness. By means of the stopper the rod element can tightly be arranged in a respective barrel body or dosage chamber. Like this, an underpressure, partial vacuum or vacuum can be induced in the dosage chamber which allows for the drawing of liquid into the dosage chamber.

Rotating the shell and the rod element relative to each other can be embodied by either the shell rotating around the rod element, the rod element rotating in the shell or the shell and the rod element both rotating. For an efficient appropriate rotational movement the shell and the rod element can be coaxially arranged.

The term "travel along each other" as used in connection with the first and second thread arrangements can relate to a part being moved or shifted in or on the thread. For example, a male member such as a pin can be moved in and along a groove of a female thread.

The term "inclination angle" as used in the context of the invention relates to an angle between the thread and a plane perpendicular to the longitudinal axis of the stem of the rod element or of the shell.

The stem of the rod element can have the shape of a post or cylinder. While extending into the interior of the housing the distal end of the body of the rod element can lie close to the distal end of the housing and the proximal end of the stem of the rod element can lie close to the proximal end of the housing.

The shell can be arranged at least partially around the rod element or at least around its section where the first thread arrangement is located. It can be embodied as a hollow cylinder or it can comprise one or plural cylinder segments which, for example, together can form a hollow cylinder. In particular, it can consist of two essentially half-cylindrical walls or clamshells.

The dosing device can be made of a plastic material. In particular, it can be made of a sterilisable plastic material which can be manufactured in an injection molding process.

The dosing device can be integrated in another device requiring dosing functionality. For example it can be integrated in a medical delivery device such as an injection device. Furthermore, it can also itself be the medical delivery device or injection device.

By varying the inclination angle along the thread specific dosing features can be implemented. In particular, it can be achieved that throughout the whole dosing process different volumes are dosed per rotation of the rod element and the shell relative to each other. For example, when the inclination angle is comparably big the rod element is comparably rapidly moved in the axial direction and the change of the volume of the dosage chamber is also comparably rapidly changed when the first and second thread arrangement travel along each other at the respective section of the thread with the comparably big inclination angle. Similarly, when the inclination angle is comparably small the change of the volume of the dosage chamber is also comparably small when the first and second thread arrangements travel along each other at the respective section of the thread with the comparably small inclination angle. Thus, the thread can exactly be shaped to suit a preferred dosing behaviour. For example, in an application where dosages are desired in a specific range the thread can be shaped such that it has a comparably big inclination angle in the beginning which flattens when the volume of the dosage chamber approaches the specific range. Like this, it can be achieved that a comparably large uncritical amount can quickly be dosed by the comparably big inclination angle and at the target range the dosage can be precisely adjusted by the comparably small inclination angle.

Furthermore, varying the inclination angle along the thread allows for quickly removing or reducing air out of the dosing device or controlling the air volume in the dosing device. In particular, when providing a comparably steep inclination at the beginning of the thread the air can be quickly handled before dosing of the liquid starts. Like this, the air in the system can be controlled and it can be achieved that no priming is necessary before starting delivery of the dosed liquid. Concomitantly, the fluid can be precisely dosed once the thread is in a flatter section, i.e. after the air is handled. Like this, a precise and convenient dosing of a liquid out of a container is possible. In particular, the dosing device according to the invention can allow for efficiently dosing a comparably small volume out of a comparably large container.

These and other dosing applications or dosing properties can be realized by means of the varying inclination angle.

The first thread arrangement can be an outer thread arrangement and, correspondingly, the second thread arrangement can be an inner thread arrangement. The term "outer" in connection with the thread arrangement can relate to a direction into which the thread arrangement is oriented. In particular, it can relate to a thread arrangement being outwardly oriented such that it can interact with a corresponding inner thread arrangement. Similarly, the term "inner" in connection with the thread arrangement can relate to an opposite direction into which the thread arrangement is oriented.

The dosing device can comprise a delivery orifice which can be shaped for a particular application or administration of a medicament to be delivered from the device. For example, it can be a needle if the device is intended for injecting the medicament. In such an embodiment the delivery orifice or needle can extend from the interior of the housing through its proximal opening out of the housing or a specific part thereof. The delivery orifice can also be adapted for being connected to a delivery member. For example, it can comprise a male or female part of a Luer lock or Luer taper connector and the delivery member can be equipped with a corresponding female or male Luer lock connector. Other examples of delivery orifices are nozzles, valves, fluid guides or the like.

The term "axial force" as used in connection with moving the rod element, when the dosing device is in the delivery status, can relate to a force applied to the rod element in order to axially move it. Typically such axial force can be manually induced, e.g. by pushing with a thumb on the distal end of the rod element or on a container mounted to the rod element or on another part connected to the rod element.

In this connection the term "prevent" can relate to impeding the axial force to axially move the rod element. It is understood that if the axial force is high enough the rod element could still be axially moved, e.g., by breaking or deforming certain parts or features of the device. Thus, preventing the axial movement by an axial force can relate to a proper use of the device.

Preferably, the dosing device further comprises a housing having an interior, a proximal opening and a distal opening, wherein the rod element extends into the interior of the housing, the shell extends into the interior of the housing and the dosage chamber is formed in the interior of the housing.

The term "proximal" as used in connection with the invention can relate to an orientation of the dosing device or particular parts thereof which in its intended use is directed to a body of the patient. Thereby, proximal portions or parts can be directed to or positioned closer to the body of the patient when the dosing device is applied to the patient. Contrary, the term "distal" as used in connection with the invention and the disclosed embodiments thereof can relate to an orientation of the dosing device which in its intended use is directed away from the body of the patient. For example, in a conventional syringe the proximal end usually is the tip of the needle and the distal end is the end of the plunger where the thumb is to be laid.

The optional housing can be more or less cylindrically shaped. The distal and proximal openings can be embodied at respective distal and proximal end sides of the housing. It can have a flange portion as finger rest at or near its distal end in which the distal opening is arranged. The housing can particularly form an outer envelope of the dosing device. It can be shaped to allow a convenient handling and use of the device as well as to protect the components in its interior.

The term "extend into" in connection with the rod element, the shell, the housing and other parts can relate to being fully or partially arranged inside. It can, for example, relate to an arrangement where a portion of a part is partially outside another part but projects into the other part.

Preferably, in the dosing device one of the first thread arrangement of the rod element and the second thread arrangement of the shell is a male thread arrangement with at least one male member, the other one of the first thread arrangement of the rod element and the second thread arrangement of the shell comprises the thread, wherein the at least one male member of the male thread arrangement projects towards the thread and the thread is dimensioned to receive the at least one male member of the male thread arrangement. The male member of the male thread arrangement can be a pin. Thereby, in a dosing status, the male member can travel along the thread when rotating the shell relative to the rod element. The thread can be embodied as an outer thread, e.g., on the stem of the rod element or as an inner thread on the inner surface of the shell.

Preferably, the thread of the first thread arrangement of the rod element or the second thread arrangement of the shell has a start point and an end point and the inclination angle of the thread of the first thread arrangement of the rod element or the second thread arrangement of the shell near the start point of the thread is bigger than near the end point of the thread. The term "near" as used in this connection can relate to being located close to the start or and point. In particular, it can be the section of the thread adjacent to the start or end point. By designing the thread steeper near the start point the effects described above with regard to air control and dosing behaviour can efficiently be achieved.

Thereby, the thread of the first thread arrangement of the rod element or the second thread arrangement of the shell comprises a priming section starting at the start point of the thread and a dosing section ending at the end point of the thread, wherein the inclination angle of the thread in the priming section is bigger than the inclination angle of the thread in the dosing section. Such an arrangement of the thread can particularly be beneficial to control the initial air in the system and to bypass the need of a priming step.

Preferably, the thread of the first thread arrangement of the rod element or of the second thread arrangement of the shell is equipped with a plurality of irregularities. Such irregularities can induce an audible and/or tactile signal each time the first thread arrangement and the second thread arrangement pass by them, i.e. at a certain rotation. The irregularities can be gaps or grooves in the walls of the thread or the like.

Thereby, the irregularities of the thread of the first thread arrangement of the rod element or of the second thread arrangement of the shell preferably are positioned at a fixed distance to each other. For example, the thread can comprise ten irregularities per full turn. By arranging the irregularities at a fixed distance to each other, the user of the dosing device can be provided with the signal each same rotation. This allows for convenient dosing providing specific information via the signal to the user.

Preferably, the priming section of the thread of the first thread arrangement of the rod element or the second thread arrangement of the shell is arranged between the start point of the thread and a first irregularity adjacent to the start point. Like this, the air volume in the system can be controlled and removal as a pre-dosing step can be provided within one click signal such that the user is informed about the status of the dosing. This allows for a convenient and controllable dosing procedure.

Thereby, in the dosing section of the thread of the first thread arrangement of the rod element or the second thread arrangement of the shell, the irregularities preferably are located such that rotating the shell about a predefined rotating angle causes the dosage chamber to change by a predefined volume. Like this, the user can control the amount of liquid dosed without visual control. For example, the predefined volume can be 25 µl such that when the user rotates from one click to the next he knows that 25 µl are dosed or removed from the dosage chamber.

In the dosing device, when rotating the shell and the rod element relative to each other, the first thread arrangement of the rod element and the second thread arrangement of the shell repeatedly interact with the plurality of irregularities at a predefined rotating angle corresponding to the distance between two adjacent irregularities. Particularly, each rotation about the predefined angle can change the volume of the dosage chamber by a constant or varied predefined amount. Like this a clear signal can be provided to a user of the dosing device during dosing indicating that the dosage volume has been changed by the predefined amount.

Preferably, the rod element comprises a transfer channel which extends through the stem along the longitudinal axis of the stem. The transfer channel allows for establishing a connection through the rod element and particularly axially through the stem thereof. It can be embodied as a transfer needle. In particular, a container arranged at or near the distal end of the rod element can be connected to the dosage chamber via the transfer channel. The transfer channel allows for transferring a liquid from the container through the rod element into the dosage chamber when the shell is rotated relative to the rod element. More specifically, by rotating the rod element is moved along the longitudinal axis such that the dosage chamber is enlarged or reduced and liquid is transferred from the container into the dosage chamber or vice versa.

The term "container" as used herein can relate to any liquid reservoir suitable for storing and transporting a liquid. Where the liquids are medicaments or the like, the container can particularly be a vial. The term "vial" as used in this connection can relate a comparably small vessel or bottle, commonly used to store pharmaceutical products or pharmaceuticals or medicaments in liquid, powdered or capsule form. The vial can be made of a sterilisable material such as glass or plastic such as, e.g., polypropylene.

Preferably, the dosing device comprises a container seat connected to the distal end of the stem of the rod element. Such a container seat allows for connecting a container at a well-defined position and orientation. This allows for an efficient coupling of the container to the system.

Thereby, the transfer channel preferably comprises a tip and an opening wherein, in the dosing status of the dosing device, the tip and the opening project into the container seat such that they are located inside a container when the container is arranged in the container seat. The transfer channel can be a transfer needle. The container can be closed by a penetrable cover such as a septum, a cap or the like. By means of the transfer channel an axial connection of the container to the rod element is possible and it can be linearly coupled to the dosage chamber which allows for an efficient implementation.

Preferably, the transfer channel connects the container seat with the dosage chamber such that, when a container with a fluid is arranged in the container seat and the rod element is moved along the longitudinal axis of its stem orifice by rotating the shell relative to the rod element in a first direction of rotation, the fluid is transferred from the container to the dosage chamber. This allows for an efficient design of the delivery device.

Furthermore, the shell and the transfer channel preferably are arranged such that, when the container is arranged in the container seat and the rod element is moved along the longitudinal axis of its stem by rotating the shell relative to the rod element in a second direction of rotation opposite to the first direction of rotation, the fluid is transferred from the dosage chamber to the container. This allows for an increasing as well as decreasing dose selection. The dosage in the dosing chamber can, thus, conveniently be varied, adjusted and corrected back and forth until a precise amount of liquid is dosed.

The dosing device preferably comprises a counter coupled to the rod element such that the counter indicates a volume of the dosage chamber formed by the rod element when being moved along the longitudinal axis of its stem by rotating the shell around the stem of the rod element. By coupling the counter to the rod element a movement of the latter in relation to the delivery orifice can be identified and directly reflected by adjusting the displayed number corresponding to the dosage volume or selected dose. Like this, an efficient implementation of a precise and purely mechanical dosage counter is possible.

Thereby, the counter preferably decouples from the rod element upon changing the dosing device from a dosing status to a delivery status. Like this, the displayed selected dose can remain indicated during and after delivery. This allows for providing a purely mechanical marker to record the administered volume of liquid.

BRIEF DESCRIPTION OF THE DRAWINGS

The dosing device according to the invention is described in more detail hereinbelow by way of an exemplary embodiment and with reference to the attached drawings, in which:

FIG. 4 shows a front view of the injection device of FIG. 1 in the dosing status after dosing;

FIG. 5 shows a cross sectional view of the injection device of FIG. 4;

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
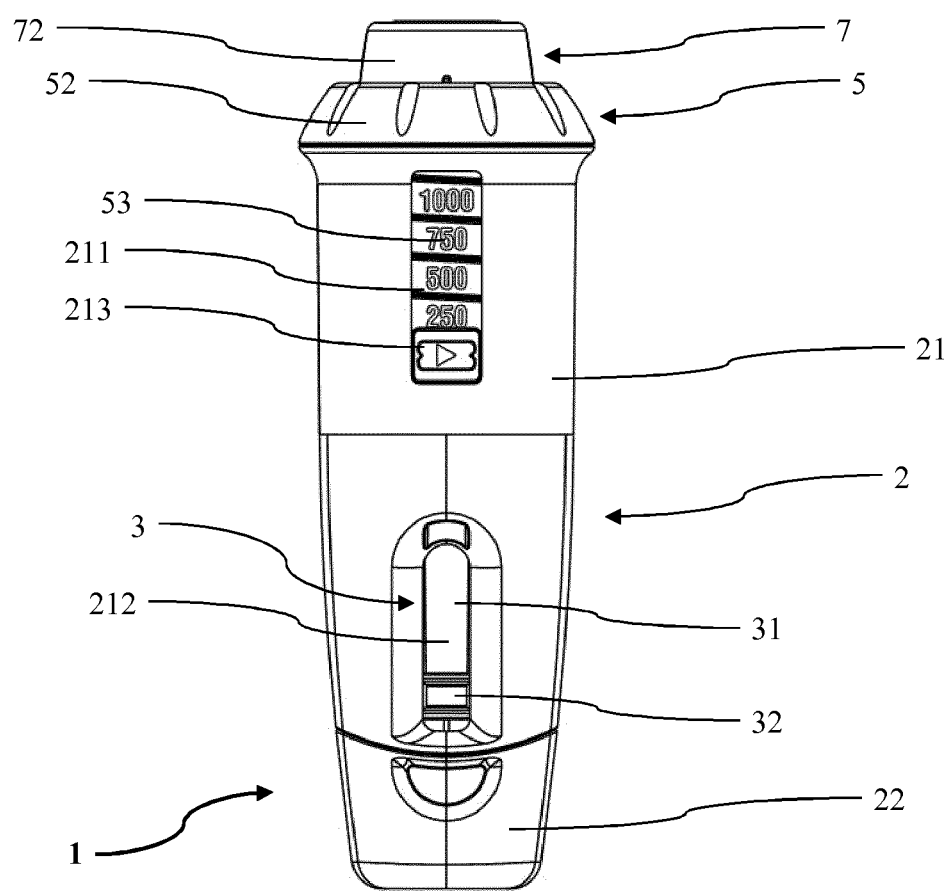
FIG. 1 shows a front view of a start position of an injection device as an embodiment of a dosing device according to the invention in a dosing status.

FIG. 1 shows an injection device 1 as an embodiment of a dosing device according to the invention in a dosing status. The injection device comprises a housing 2 with a body 21 and a needle shield 22. The body 21 has an interior, a top distal opening and a bottom proximal opening. It is further equipped with an indicator window 211 in an upper part and a chamber window 212 vertically below the indicator window.

In the interior of the body 21 a rod element 3 with a vertically aligned stem 31 and a rubber stopper 32 at the lower end of the stem 31 are arranged. The rubber stopper 32 and a lower part of the stem 31 are visible through the chamber window 212 of the body 21 of the housing 2.

Through the distal opening of the housing 2 a dosing activator 5 extends into the interior of the body 21. The dosing activator 5 comprises a gripping ring 52 which is positioned outside the housing 2 and which laterally overlaps the distal opening of the hosing 2. As explained in more detail below, the dosing activator 5 has a dosage marking 53 as part of a counter for indicating an amount or volume of a medicament dosed. In the start position shown in FIG. 1 no medicament is dosed such that no volume is indicated in a highlighting element 213 of the indicator window 211. Rather, an arrow indicating the direction of rotation for dosing, i.e. an anti-clockwise direction, is visible through the highlighting element 213 of the indicator window 211. The dosage marking 53 and the highlighting element together are comprised by the counter of the injection device 1.

Also through the distal opening of the housing 2 a switch activator 7 extends into the interior of the body 21 and into the dosing activator 5. The switch activator 7 comprises a gripping ring 72 which is positioned outside the housing 2 and the dosing activator 5.

Figure 2:
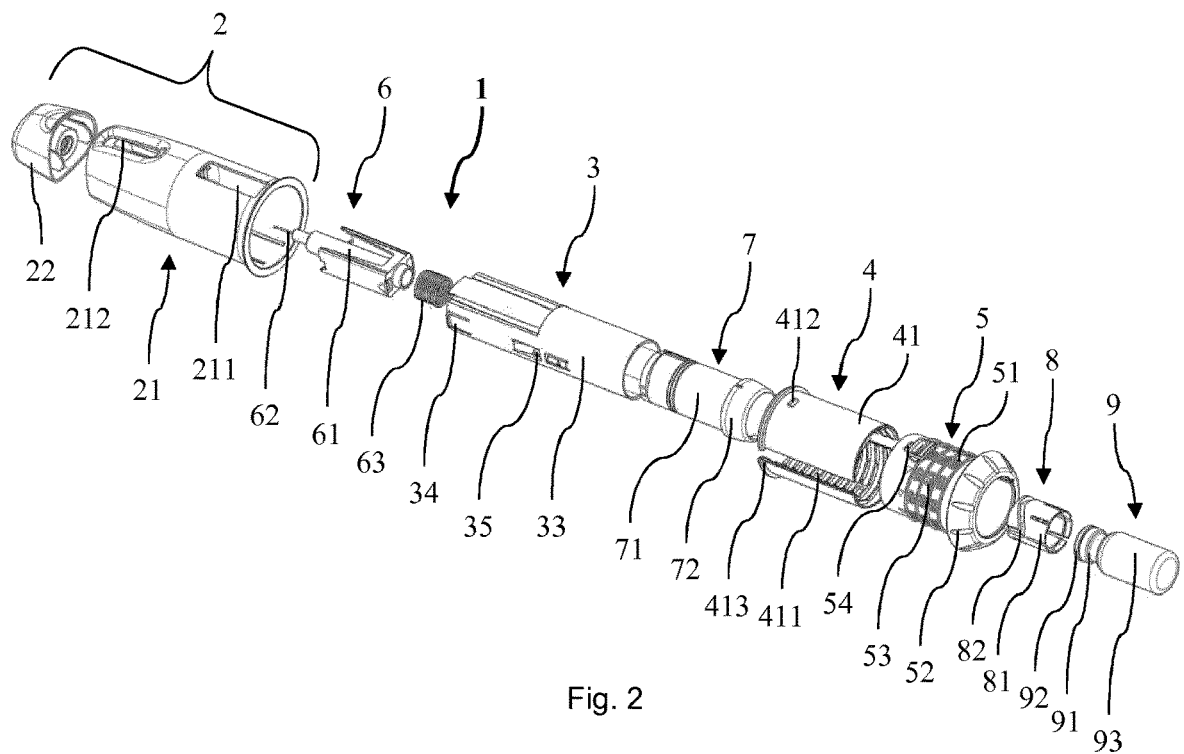
FIG. 2 shows a perspective exploded view of the injection device of FIG. 1.

In FIG. 2 the injection device 1 is shown in an exploded view such that single parts are visible. The injection device 1 is designed to receive a vial 9 as a container. In a common manner the vial 1 has a body 93 and a neck 91 which is closed by a cap 92. In the interior of the body 93 a liquid medicament is stored which is to transfer, dose and deliver or inject by means of the injection device 1.

The rod element 3 comprises a cylinder portion 33 which is sized to about half length of the rod element, i.e. the right hand half of it in FIG. 2. The cylinder portion 33 has a hollow interior dimensioned to receive a cylinder portion 71 of the switch activator 7. The switch activator 7 also essentially is cylindrical and has a hollow interior which is shaped to receive the vial 9 and a vial seat 8 as a container seat. The vial seat 8 has a neck holder 81 and a cylindrical outer surface provided with a hub groove 82.

The rod element 3 is equipped with two opposite pins 35 as male members of an outer or first thread arrangement. The pins 35 radially project off the rest of the rod element 3. The pins 35 are to a certain extent flexibly mounted in order to allow to be forced inwardly, i.e. into the direction of a longitudinal axis of the rod element 3. The rod element 3 further comprises two opposite limiting fins 34 positioned near a proximal end of the rod element 3.

The medical injection device 1 further comprises a dial shell 4 as shell having two half-cylindrical clamshells 41. On the inner surfaces, both clamshells 41 are equipped with thread sections wherein the tread sections of the clamshells 41 are formed to build two parallel continuous threads 411 as inner or second thread arrangement when the clamshells 41 are put together forming a cylinder. At the proximal ends the clamshells 41 are provided with an outwardly extending flange 413. Further, each of the clamshells 41 is equipped with a rim segment 412 radially or outwardly projecting off the outer surface. The clamshells 41 are dimensioned to fit around the cylinder portion 33 of the rod element 3.

The dosing activator 5 has a cylindrical body 51 with a hollow interior, wherein the dosage marking 53 is provided at and around an outer surface of the cylindrical body 51. The gripping ring 52 forms a distal end of the dosing activator 5. In the cylindrical body 51 a pair of recesses 54 corresponding to the rim segments 412 of the clamshells 41 is arranged. The dosing activator 5 is dimensioned to be arranged around the clamshells 41 such that the rim segments 412 engage the recesses 54 and fix the dial shell 4 to the dosing activator 5 when being arranged around the cylinder portion 33 of the rod element 3.

Between the stem 31 of the rod element 3 and the proximal opening of the body 21 of the housing 2 a dosage member 6 is arranged. The dosage member 6 has a spring 63, a chamber cylinder 61 and a delivery needle 62 as a delivery orifice of the injection device 1. The chamber cylinder 61 is dimensioned such that the stem 31 and the rubber stopper 32 of the rod element 3 fit into it.

Figure 3:
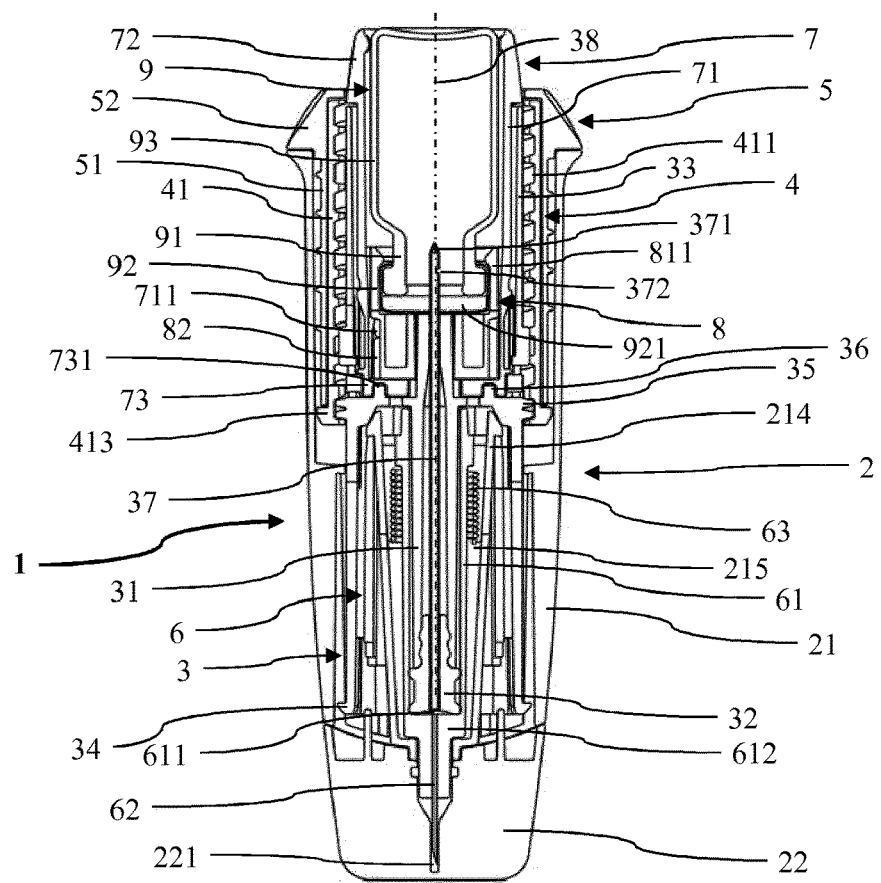
FIG. 3 shows a cross sectional view of the injection device of FIG. 1 in the dosing status while being in the start position.

FIG. 3 shows the assembled injection device 1 in the start position. The injection device 1 is presented in an upright alignment such that the proximal end is at the bottom and the distal end at the top. As described above, the switch activator 7 extends inside the hollow interior of the cylinder portion 33 of the rod element 3. Thereby, the cylinder portion 71 of the switch activator 7 is inside the rod element 3 and the grip portion 72 of the switch activator 7 upwardly projects out of the rod element 3. More particularly, the grip portion 71 of the switch activator 7 is dimensioned such that it does not fit into the cylinder portion 33 of the rod element 3 but abuts a distal opening thereof.

Inside the hollow interior of the switch activator 7 the vial seat 8 is positioned at a bottom 73 of the switch activator 7. A hub protrusion 711 inwardly projects from the inner surface of the cylinder portion 71 of the switch activator 7 into the direction of the vial seat 8. The hub protrusion 711 engages the hub groove 82 of the vial seat 8 such that the switch activator 7 and the vial seat 8 can interact as described in more detail below.

The rod element 3 has a central longitudinal axis 38 which in FIG. 3 vertically extends. The longitudinal axis 38 of the rod element 3 corresponds to longitudinal axes of the housing 2, the dial shell 4, the dosing activator 5, the dosage member 6, the switch activator 7, the vial seat 8, the vial 9 and the overall device 1.

The rod element 3 further has a transfer needle 37 which centrally passes through the stem 31 and the rubber stopper 32. The stem 31 upwardly extends into the interior of the cylinder portion 33 and into the vial seat 8. Thereby, the stem 31 is torque-resitantly connected to the vial seat 8 by interacting form-fitting parts. The transfer needle 37 extends from a bottom or proximal end of the rubber stopper 32 axially through the rubber stopper 32 and the stem 31 and projects above the top or distal end of the stem 31 ending in a sharp tip 371. Downwardly, the stem 31 extends into the chamber cylinder 61 of the dosage member 6.

The rubber stopper 32 is clamped by the stem 31 such that it is arranged at the bottom or proximal end of the stem 31. Thus, the rubber stopper 32 is located fully inside the chamber cylinder 61 of the dosage member 6 wherein, in the start position shown in FIG. 3, the rubber stopper 32 abuts a bottom 612 of the chamber cylinder 61. The proximal end of the rubber stopper 32 is concave such that between the rubber stopper 32 and the bottom 612 of the chamber cylinder 61 a minimal dosage chamber 611 is formed inside the chamber cylinder 61. The bottom 612 of the chamber cylinder 61 has a downwardly extending post and is provided with the delivery needle 62 which projects through the post. The bottom or proximal end of the delivery needle 62 is received in a seal channel 221 of the needle shield 22 of the housing such that the delivery needle 62 is covered, protected and sealed.

The neck holder 81 of the vial seat 8 has a retaining formation 811 which comprises vertical slits and an inwardly extending flange end. In a step of preparing the injection device 1, the vial 9 is pressed top down into the switch activator 7 and the vial seat 8. Thereby, the vertical slits allow the retaining formation 811 to be sufficiently moved in an outward direction such that a head of the vial 9 with the cap 92 passes the flange end of the retaining formation 811. Once the vial 9 is sufficiently pressed down, the flange end of the retaining formation 811 snaps behind the head and in the neck 91 of the vial 9 such that the vial 9 is held. In this way, the vial 9 is vertically mounted top down in the delivery device 1 with its cap 92 abutting the distal end of the stem 31 of the rod element 3. At the top distal opening of the switch activator 7 a protrusion inwardly projects which fits and guides the exterior of the body 93 of the vial 9.

While the vial 9 being pressed into the vial seat 8 the tip 371 of the transfer needle 37 penetrates the cap 92 including a septum 921. The tip 371 forms the top or distal end of the transfer needle 37. When the vial 9 is completely snapped in the vial seat 8 the transfer needle 37 extends into the interior of the vial 9. Close to the tip 371 but slightly below it a sideward opening 372 is provided in the transfer needle 37. In the start position shown in FIG. 3, the transfer needle 37 forms an open duct as transfer channel between the interior of the vial 9 and the dosage chamber 611 of the dosage member 6.

The pins 35 of the outer thread arrangement of the rod element 3 horizontally project from the rest of the rod element 3 to the left and to the right into the inner threads 411 of the dial shell 4 formed by the two clamshells 41. Thereby, the pins 35 engage the inner threads 411. The outer thread arrangement of the rod element 3 further comprises two projections 36 of a disengaging structure of a switching mechanism which are located close to the pins 35 and which axially extend into an upward direction. Each of the projections 36 engages a guidance groove 731 of the disengaging structure of the switching mechanism embodied in the bottom 73 of the switch activator 7. The guidance grooves 73 run in a plane perpendicular to the longitudinal axis 38 of the stem 31 of the rod element 3. They helically extend on the bottom 73 and are continuously approaching a centre of the bottom 73.

The body 21 of the housing 2 further comprises a bottom 213 with an opening through which the post of the bottom 612 of the chamber cylinder 61 of the dosage member 6 extends into the needle shield 22. From the bottom 213 of the body 21 two retaining arms 214 and a spring rest 215 upwardly extend into the interior of the body 23. Thereby, the two retaining arms 214 are snapped behind a corresponding skirt of the dosage member 6. The helical spring 63 is clamped between the spring rest 215 and a horizontal surface of the dosage member 6. Thus, the dosage member 6 is connected to the body 21 of the housing 2 by the retaining arms 214 wherein the spring 63 is pre-stressed between the body 21 and the dosage member 6.

FIG. 4 and FIG. 5 show the injection device 1 after dosing, i.e. after transferring 200 µl of the medicament from the vial 9 into the dosage chamber 611. As indicated by the arrow in FIG. 4, for dosing the dosing activator 5 is rotated anti-clockwise relative to the housing 2. Thereby, the housing 2 can be held at its body 21 by one hand of a patient and with the other hand the patient can rotate the gripping ring 52 of the dosing activator 5 relative to the housing 2. Since the clamshells 41 of the dial shell 4 are connected to the dosing activator 5 in a torque-resistant manner by the rim segments 412 projecting into the recesses 54, the dial shell 4 is rotated together with the dosing activator 5. In the meantime the rod element 3 is torque-resistantly connected to the housing 2 via the dosage member 6 and the retaining arms 214 of the housing 2 such that it is non-rotatable about its axis 38. Thus, the dial shell 4 rotates around the rod element 3 causing the pins 35 to travel along the threads 411. Like this, the rod element 3 is upwardly moved along the longitudinal axis 38 of the stem 31.

When axially moving the rod element 3 in an upward direction, the dosing chamber 611 between the rubber stopper 32 and the bottom of the chamber cylinder 61 of the dosage member 6 increases. In the meantime, an underpressure is created in the dosing chamber 61 such that the medicament is drawn from the vial 9 through the transfer needle 37 into the dosing chamber 611.

When the dosing activator 5 rotates relative to the housing 2 during dosing, the number visible in the highlighting element 213 of the indicator window 211 changes in correspondence with the volume of the dosing chamber 611. More particularly, the highlighting element 213 is on one hand guided in the indicator window 211 such that it is axially or vertically movable relative to the body 21 of the housing 2 but not tangentially. On the other hand the outer surface of the body 51 of the dosing activator 5 is provided with a thread rib which is connected to the highlighting element 213 via a corresponding groove. Thus, when the dosing activator 5 rotates relative to the housing 2, the highlighting element 213 is vertically moved by the thread rib interacting with groove. Compared to FIG. 1 in which the highlighting element 213 is at the bottom end of the indicator window 211, in FIG. 4 it is upwardly moved and lies over the numeral 200 of the dosage marking. This indicates that 200 µl of the medicament are dosed in the dosage chamber 611.

When being in the dosing status, the dosing activator 5 can be rotated in both directions. Thereby, an anti-clockwise rotation causes the dosage volume 611 to increase and, vice versa, a clockwise rotation causes the dosage volume 611 to decrease such that the medicament is transferred back to the vial 9.

Figure 6:
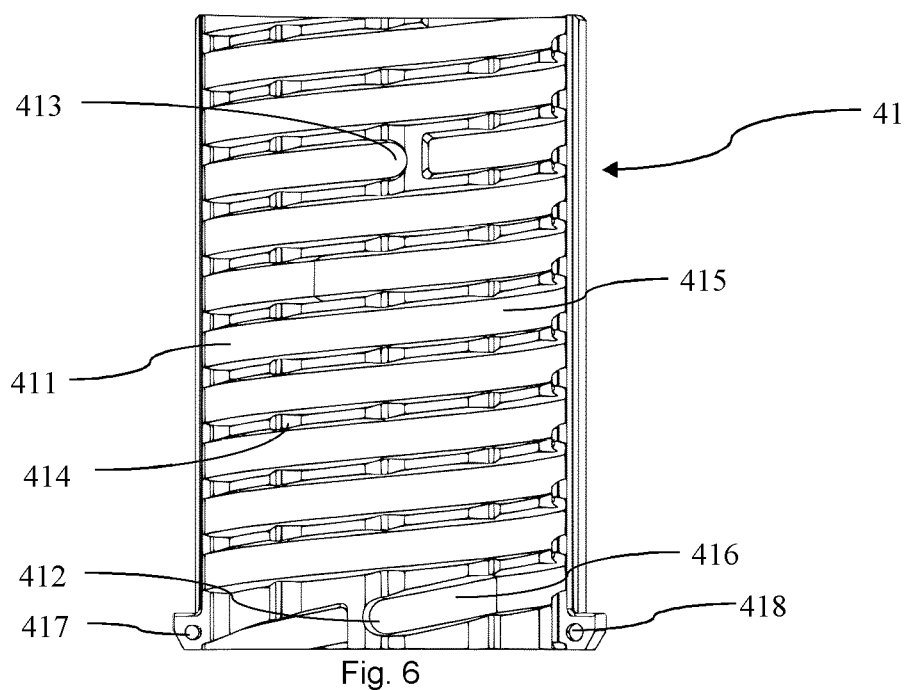
FIG. 6 shows a front view of a clamshell of a dial shell of the injection device of FIG. 1.

In FIG. 6 one of the two identical clamshells 41 is shown wherein an interior surface of the clamshell 41 is visible. The inner surface is provided with half sections of the two independent threads 411. Laterally at a bottom section the clamshell 41 is provided with a connection stud 417 on the left side and a corresponding connection hole 418 on the right side. When the two clamshells 41 are mounted together, the connection studs 417 are plugged into the connection holes 418 such that a hollow cylinder is formed. The half sections of the threads 411 of the two clamshells 41 match such that the two threads 411 continuously extend in parallel at the inner surface of the cylinder.

Each of the threads 411 comprises a lower start point 412 and an upper end point 413. The start point 412 and the end point 413 limit the path of travel along which the respective pin 35 can be moved inside the thread 411. The threads 411 are provided with gaps 414 as irregularities. The gaps 414 are distributed along the threads 411 such that the pins 35 travelling between two adjacent gaps causes the dosage chamber 611 to change by a predefined volume of 25 µl. When the pins 35 pass opposite gaps 414 of the threads 411 a click signal is induced which can be heard and felt. Thus, when the patient rotates the dosing activator 5 and notices a click he knows that the dosed volume of medicament has changed by 25 µl. One turn of the threads 411 is provided with ten gaps 414. Thus, the gaps 414 are separated by a predefined angle of, e.g., 36° from each other. In other embodiments, the gaps 414 can also be irregularly distributed such that variable rotation angles are provided between two click and correspondingly variable dose increments are possible.

Figure 7:
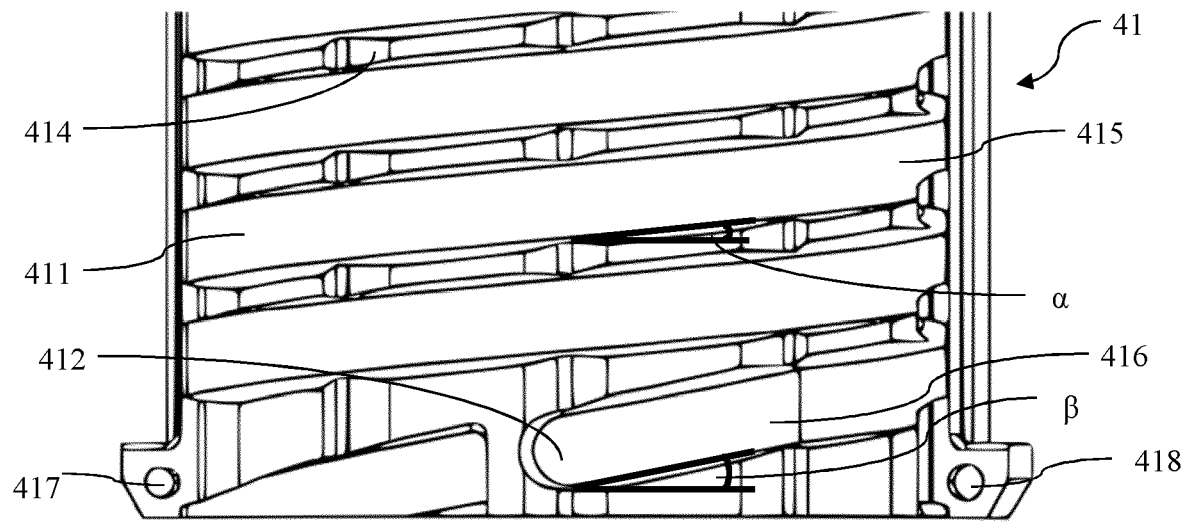
FIG. 7 shows a detail of the view of FIG. 6.

Each of the threads 411 is equipped with a priming section 416 and with a dosing section 415. As can be best seen in FIG. 7 the dosing sections have a first inclination angle β and the priming sections 416 have a second inclination angle β. The second inclination angle β is bigger than the first inclination angle α such that the priming section 416 is steeper than the dosing section 415. At the first gaps 414 adjacent to the start point 412 the priming sections 416 pass over into the dosing sections 415 and the respective inclination angles change.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the FIGS. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:
1. A dosing device, comprising:
   a rod element having a stem with a longitudinal axis and a first thread arrangement; and
   a shell having a second thread arrangement,
   wherein,
   the first thread arrangement of the rod element or the second thread arrangement of the shell comprises a thread,
   the first thread arrangement of the rod element and the second thread arrangement of the shell engage,
   the rod element is movable along the longitudinal axis of the stem by rotating the shell and the rod element relative to each other causing the first thread arrangement of the rod element and the second thread arrangement of the shell to travel along each other,
   a dosage chamber is formed by moving the rod element along the longitudinal axis of its stem,
   a volume of the dosage chamber is adapted by moving the rod element along the longitudinal axis of the stem, and
   an inclination angle of the thread of the first thread arrangement of the rod element or the second thread arrangement of the shell varies along the thread of the first thread arrangement of the rod element or the second thread arrangement of the shell.

2. The dosing device according to claim 1, further comprising:
   a housing having an interior, a proximal opening and a distal opening, wherein the rod element extends into the interior of the housing, the shell extends into the interior of the housing and the dosage chamber is formed in the interior of the housing.

3. The dosing device according to claim 1, in which one of the first thread arrangement of the rod element and the second thread arrangement of the shell is a male thread arrangement with at least one male member, the other one of the first thread arrangement of the rod element and the second thread arrangement of the shell comprises the thread, wherein the at least one male member of the male thread arrangement projects towards the thread and the thread is dimensioned to receive the at least one male member of the male thread arrangement.

4. The dosing device according to claim 1, wherein the thread of the first thread arrangement of the rod element or the second thread arrangement of the shell has a start point and an end point and the inclination angle of the thread of the first thread arrangement of the rod element or the second thread arrangement of the shell near the start point of the thread is bigger than near the end point of the thread.

5. The dosing device according to claim 4, wherein the thread of the first thread arrangement of the rod element or the second thread arrangement of the shell comprises a priming section starting at the start point of the thread and a dosing section ending at the end point of the thread, wherein the inclination angle of the thread in the priming section is bigger than the inclination angle of the thread in the dosing section.

6. The dosing device according to claim 5, wherein the thread of the first thread arrangement of the rod element or of the second thread arrangement of the shell is equipped with a plurality of irregularities.

7. The dosing device according to claim 6, wherein the irregularities of the thread of the first thread arrangement of the rod element or of the second thread arrangement of the shell are positioned at a fixed distance from each other.

8. The dosing device according to claim 7, wherein the priming section of the thread of the first thread arrangement of the rod element or the second thread arrangement of the shell is arranged between the start point of the thread and a first irregularity adjacent to the start point.

9. The dosing device according to claim 6, in which, when rotating the shell and the rod element relative to each other, the first thread arrangement of the rod element and the second thread arrangement of the shell repeatedly interact with the plurality of irregularities at a predefined rotating angle corresponding to a distance between two adjacent irregularities.

10. The dosing device according to claim 9, wherein, in the dosing section of the thread of the first thread arrangement of the rod element or the second thread arrangement of the shell, the plurality of irregularities are located such that rotating the shell about a predefined rotating angle causes the dosage chamber to change by a predefined volume.

11. The dosing device according to claim 1, wherein the rod element comprises a transfer channel which extends through the stem along the longitudinal axis of the stem.

12. The dosing device according to claim 11, comprising a container seat connected to a distal end of the stem of the rod element.

13. The dosing device according to claim 12, wherein the transfer channel comprises a tip and an opening, and wherein, in a dosing status, the tip and the opening project into the container seat such that they extend into a container when the container is arranged in the container seat.

14. The dosing device according to claim 1, comprising a counter coupled to the rod element such that the counter indicates a volume of the dosage chamber formed by the rod element when being moved along the longitudinal axis of the stem by rotating the shell around the stem of the rod element.

15. The dosing device according to claim 14, wherein the counter decouples from the rod element upon changing the dosing device from a dosing status to a delivery status.

16. The dosing device according to claim 1, wherein the thread of the first thread arrangement of the rod element or of the second thread arrangement of the shell is equipped with a plurality of irregularities.

17. The dosing device according to claim 16, in which, when rotating the shell and the rod element relative to each other, the first thread arrangement of the rod element and the second thread arrangement of the shell repeatedly interact with the plurality of irregularities at a predefined rotating angle corresponding to a distance between two adjacent irregularities.

18. The dosing device according to claim 1, comprising a container seat connected to a distal end of the stem of the rod element.

* * * * *